United States Patent [19]

Loesser, III

[11] 4,027,985

[45] June 7, 1977

[54] COMPRESSIBLE DISPENSING CONTAINER HAVING PIERCING PRONGS

[76] Inventor: Ernest W. Loesser, III, 5 Dalewood Drive, Cedar Grove, N.J. 07009

[22] Filed: June 16, 1975

[21] Appl. No.: 587,066

[52] U.S. Cl. .............................. 401/134; 401/196; 222/85; 222/106; 128/269

[51] Int. Cl.² .................. A61M 35/00; B05C 21/00

[58] Field of Search ......... 222/81, 83, 83.5, 85–86, 222/88–89, 105–106, 192; 128/269; 401/132–134, 196

[56] References Cited

UNITED STATES PATENTS

| | | | |
|---|---|---|---|
| 1,309,201 | 7/1919 | Hollister | 128/269 |
| 1,673,590 | 6/1928 | Redheffer | 222/106 X |
| 2,315,319 | 3/1943 | Dresden | 222/81 |
| 2,341,601 | 2/1944 | Kadt | 222/83 |
| 3,774,609 | 11/1973 | Schwartzman | 128/269 |
| 3,876,314 | 4/1975 | Nehring | 128/269 X |

Primary Examiner—Stanley H. Tolberg
Assistant Examiner—Charles A. Marmor
Attorney, Agent, or Firm—Frank P. Cyr

[57] ABSTRACT

A hermetically sealed container formed of a pliable material and which contains therein a substance capable of being ejected from within the container by application of a pressure force on the walls of the container. A band formed of a suitable material is mounted on the container at the discharge or exit end of the container, the band having a sharpened prong which is normally out of contact with one wall of the container, but which will engage with the wall of the container when pressure is applied on the walls of the container to thus cause container walls to expand and to force one of the walls into engagement with the sharpened prong to thus effect a puncturing of the wall to form an opening through which the contents of the container may be expelled.

7 Claims, 9 Drawing Figures

COMPRESSIBLE DISPENSING CONTAINER HAVING PIERCING PRONGS

BACKGROUND OF THE INVENTION

Numerous devices have heretofore been employed to form an opening in a package or container when it is desired to expel the material housed therein. However, all such prior devices have employed complicated arrangements to effect the formation of an exit opening in the container when the contents therein are to be expelled from therein.

With the above in mind, it is the primary object of the invention to provide a package or container with a simplified structure, whereby when pressure is applied against the walls of the container the materials within the container being thus displaced will cause the, the container walls to bulge outwardly, thus causing one wall thereof to engage with a sharpened prong which will pierce the same to form an exit opening in the wall of the container or package.

Another object of the invention is to provide a package or container formed of a suitable, pliable film with a band extending over one of the walls thereof, the band having a sharpened prong formed thereon which is normally out of contact with the wall with which it is associated, but which will engage with the said wall to form an exit opening when pressure is applied against the walls of the package when it is desired to expel the material from therewithin.

Another object of the invention is to mount a piercing prong on a band which can completely encircle the outlet end of the container or, whenever found more practical, the band can extend over only one wall of the container and, again the piercing prong acting to form an exit opening in the package when pressure is exerted against the walls of the container thus displacing the materials within the container and causing the walls to bulge outwardly and ultimately piercing the wall to form the exit opening.

Another object of the invention is to form a dispensing container of a suitable film-like impervious material which can be readily punctured when pressure is applied against the walls of the container.

Another object of the invention is to provide a means for storing a substance within a container which is capable of being expelled from therein when pressure is applied against the walls thereof, the application of such pressure causing the walls of the container to bulge outwardly and to engage with a piercing prong located at the exit or discharge end of the container to thus form an exit opening and continued application of pressure on the walls will cause outward flow of the packaged substance from within the container.

Another object of the invention is to mount a swab at the outlet end of a container and to retain the same in proper position on the container by means of a piercing prong carrying band which is also placed at the outlet end of the container.

These, together with various objects and features of the invention, which will become apparent as the following description proceeds, are attained by this container, preferred embodiments of which have been illustrated in the drawing, by way of example only, wherein:

DESCRIPTION OF THE PREFERRED EMBODIMENTS

Figure 1:
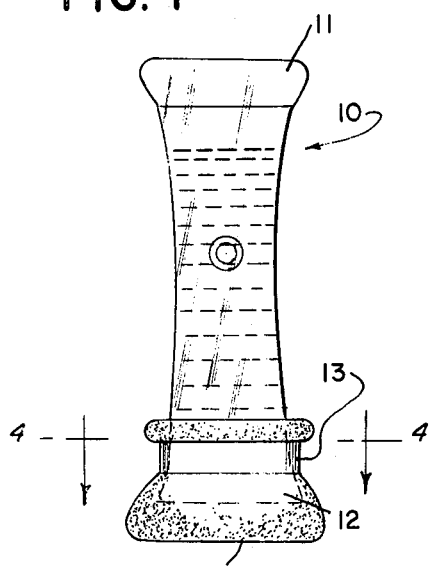
FIG. 1 is a front elevation view of a container formed in accordance with the present invention.

Referring now to the drawings wherein like reference numerals are employed to designate like parts throughout the several views thereof, numeral 10 designates generally a container or package formed of any suitable pliable material such as pliofilm, polyethylene, or other like plastic material. The only requirement for the material employed in the formation of the container is that the walls thereof may be compressed upon application of a pressure force thereon as by squeezing the same. Containers or packages of this type will preferably be employed in the packaging of small quantities or doses of a substance capable of being expelled from within the container by an application of a squeezing force on the walls thereof. Of course, a package or container of this type can be employed just as effectively in packaging larger quantities of a flowable substance.

Numeral 11 designates the upper portion or end of the container, whereas numeral 12 designates the lower portion or end. The substance packaged within the container is fed thereinto in any known manner and, following the feed of the substance within the container the ends thereof are closed as by a heat sealing operation.

Figure 7:
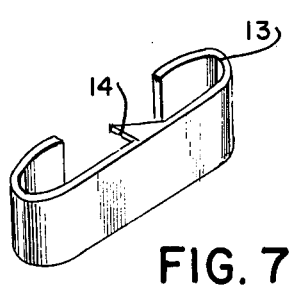
FIG. 7 is a modified type of band.

Mounted at the lower or exit end 12 of the container is a band 13 formed of any suitable material, such as metal, plastic or the like and mounted along one wall of the band is a piercing prong 14 having a sharp point formed thereon for a purpose to be described more fully hereinafter. While only one prong 14 is shown in FIGS. 3 and 7 of the drawings, it is of course obvious that as many prongs will be carried by the band as may be deemed sufficient to effect a piercing of the wall of the container.

Figure 3:
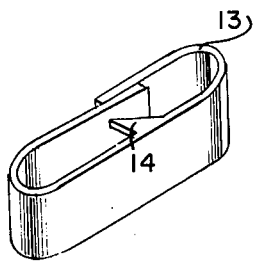
FIG. 3 shows one form of a band and piercing prong mounted thereon.
Figure 9:
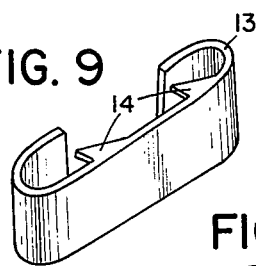
FIG. 9 is a modification of the band shown in FIG. 7.
Figure 4:
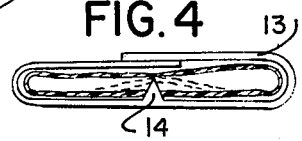
FIG. 4 is a section taken on lines 4—4 of FIG. 1, looking in the direction of the arrows.
Figure 5:
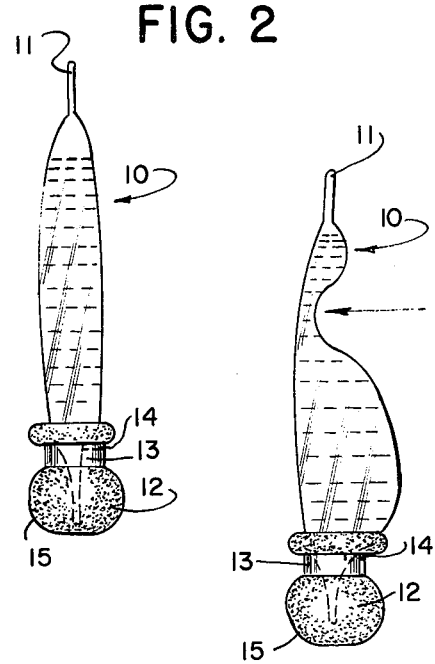
FIG. 5 is an enlarged view showing the dispensing end of the container with the swab removed therefrom.

Shown in FIGS. 3 and 4 of the drawings is a band which is designed to completely encircle the lower end of the container with the ends thereof terminating in overlapped relationships. However, is preferable or more desirable, a band constructed as shown in FIG. 7 of the drawings may be employed. The band shown in FIG. 7 of the drawings may be constructed of any suitable material such as metal, plastic, or the like and is also provided with a sharpened prong 14. It will be noted that the ends of the band do not extend into overlapped relationship as shown in FIGS. 3 and 4 of the drawings, but rather the outer ends thereof are turned inwardly and are pressed against the sides of the container to secure the same to the container.

Figure 2:
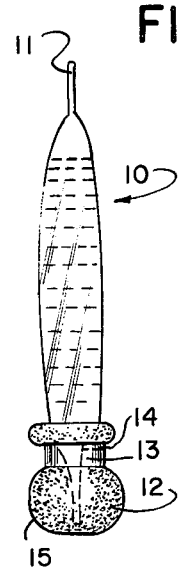
FIG. 2 is a side view thereof.

In instances where it is desirable to have a swab 15 of sponge or the like mounted at the lower end of the container, the band serves a dual purpose. The band not only serves to puncture the wall of the container, but also serves to secure and retain the swab on to the container end. An opening 16 is formed in the swab and the sealed lower end of the container is adapted to be received in this opening when the parts are in assembled relationship. To assemble the parts, the swab is first placed over the lower sealed end of the container and the band 14 applied thereover and the ends thereof bent inwardly either in the manner shown in FIGS. 1, 2 and 4 of the drawings or as shown in FIG. 7. The band 13 is sufficiently rigid so that when the ends thereof are inturned as shown in the drawings, the swab will be retained on the lower end of the container. In instances where there is no need to employ the swab, the swab may be omitted.

It will be noted that the sharpened prong is provided along the upper wall of the band. This structure permits for the application of the band along the lower sealed portion of the container with the piercing prong being located at an elevation on the container end which will permit for the same to engage with a portion of the container wall and to form an opening therein when pressure is applied to the container walls as by squeezing the same.

Figure 6:
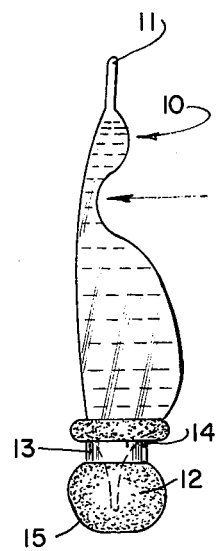
FIG. 6 is a side view of the container showing the walls of the container bulging outwardly when pressure is applied to the walls thereof.
Figure 8:
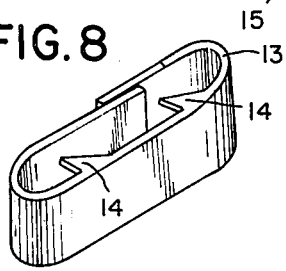
FIG. 8 is a modification of the band shown in FIG. 3.

Thus it will be apparent that the structure of the present invention provides for a simplified structure to effect the formation of an exit opening at one end of a pliable or compressible wall type container when pressure is applied against the walls thereof to thus displace the materials within the container and to cause the walls thereof to bulge outwardly as clearly shown in FIG. 6 of the drawings. The outward bulging of the walls will cause the prong on the band to pierce the wall of the container to thus form an exit opening for the materials within the container.

Changes and slight modifications in the foregoing disclosure and in some instances some features of the invention will be employed without a corresponding use of other features. Accordingly, the appended claims are to be construed broadly and in a manner consistent with the spirit and scope of the invention herein.

I claim:
1. A dispensing container for a flowable material housed therein which substantially completely fills the same, said container comprising sealed upper and lower end portions and a compressible body having a front and rear wall extending between said sealed end portions, said lower portion of said compressible body terminating in a partially collapsed area, a band having an upper and lower edge encircling a portion of said lower partially collapsed end portion area and secured thereto a piercing prong mounted on the upper edge of the said band and being directed towards the front wall only of said container adjacent said partially collapsed area, said piercing prong normally out of contact with the said front wall of said container but adapted to contact and pierce said container wall only upon application of a compressive force intermediate the upper and lower end portions of the container, said compressive force displacing the materials within the container thus causing the walls thereof to bulge outwardly whereupon said piercing prong will pierce the said wall at the partially collapsed area to form an exit opening therein and upon continued application of said compressive force on the walls of the container, the materials within the container will be expelled from therewithin through the said exit opening.

2. The structure recited in claim 1 wherein said band surrounds a swab and retains said swab on said container at the lower portion thereof.

3. The structure recited in claim 1 wherein said band surrounds the container at the lower end thereof by means of inturned ends of the band which are pressed against the side walls of said container.

4. The structure recited in claim 2 wherein an opening is provided in said swab to receive therein the lower end portion of said sealed container.

5. The structure recited in claim 1 wherein said band completely encircles the said container walls.

6. The structure recited in claim 1 wherein said band is provided with inturned ends which are pressed against the side walls of said container for securing the band to the said container.

7. The structure recited in claim 1 wherein a plurality of prongs are, provided on said band.

* * * * *